United States Patent

Heinicke

[11] Patent Number: 5,591,443
[45] Date of Patent: Jan. 7, 1997

[54] SYNERGISTIC INSECTICIDE COMPOSITION

[75] Inventor: Ralph M. Heinicke, Louisville, Ky.

[73] Assignee: Biotechnology Resources, Inc., Louisville, Ky.

[21] Appl. No.: 470,431

[22] Filed: Jun. 6, 1995

Related U.S. Application Data

[63] Continuation-in-part of Ser. No. 980,176, Nov. 23, 1992, abandoned, which is a continuation-in-part of Ser. No. 652,868, Feb. 8, 1991, abandoned.

[51] Int. Cl.⁶ .................................................. A01N 25/12
[52] U.S. Cl. .................... 424/405; 424/409; 424/418; 424/535; 514/7; 514/21; 514/775; 530/361
[58] Field of Search .................................... 424/405, 418, 424/535; 514/7, 21, 775; 530/360, 361, 832; 436/86

[56] References Cited

U.S. PATENT DOCUMENTS 4,906,616   3/1990   Gilchrist et al. ....................... 574/21

FOREIGN PATENT DOCUMENTS 4511913   4/1970   Japan .

OTHER PUBLICATIONS

Principles of Datry Chemistry Jpnness and Patton 1959 pp. 115–117, 127, 317, 326–328, 336.

*Primary Examiner*—Neil S. Levy
*Attorney, Agent, or Firm*—Anna P. Fagelson

[57] ABSTRACT

The method of making a neurotoxic insecticide which comprises:
1. Extracting a relatively heat stable, lipophilic, calcium linked, free sufhydryl, proteinaceous extract from casein, in particular the kappa casein thereof, or a casein containing material, such as skim milk, with a low molecular weight alcohol or acetone, and recovering the extract;
2. Mixing the extract with one or more membrane transfer agents, such as detergents or solvents, which allow the transfer of the protein extract across normally impermeable insect membranes, whereby the extract demonstrates neurotoxic insecticidal effects.

11 Claims, No Drawings

SYNERGISTIC INSECTICIDE COMPOSITION

REFERENCE TO RELATED APPLICATIONS

This application is a continuation-in-part of U.S. patent application Ser. No. 07/980,176 filed Nov. 23, 1992, now abandoned, which in turn is a continuation-in-part of application Ser. No. 07/652,868 filed on Feb. 8, 1991 now abandoned.

FIELD OF INVENTION

This invention pertains to a novel proteinaceous insecticidal composition of matter, the method of preparing the same and the method of application for combating insects such a aphids, red spiders, scale, caterpillars, cockroaches, fleas, ticks, slugs, etc. The composition consists of a synergistic combination of a unique type of protein prepared from casein, in particular, the kappa casein thereof, or casein containing materials, combined with an effective critical amount of an agent that will transfer this unique protein across normally impermeable membrane barriers. The protein will hereinafter be termed "dimercash", since it is a calcium linked dimer with free sulfhydryl (SH) groups.

Without the membrane transfer agent, the protein has no toxic action against insects. And at the levels employed here, the membrane transfer agents also exhibit no toxic action. However, when combined, the synergistic mixture demonstrates potent neurotoxicity. While the mixture is very effective against insects, it is harmless to animals.

BACKGROUND

The five classical groups of insecticides are: 1) inorganic stomach poisons based on heavy metals, such as mercury, arsenic, zinc and lead; 2) respiratory blocking agents, such as oils and soaps; 3) natural contact insecticides, such as pyrethrum, rotenone and nicotine; 4) volatile compounds, such as p-dichlorobenzene, hydrogen cyanide and hydrogen sulfide and 5) a wide range of modern synthetic insecticides that act on different systems in the insect. These synthetic insecticides include the various halogenated organic materials, such as DDT, Aldrin, methyl bromide, etc., and the nerve toxins such as malathion and parathion. Each of these groups has advantages and disadvantages which are well known to those skilled in the art. The disadvantage of most concern in using many of these, except perhaps for the soaps and some of the oils and natural insecticides, is their toxic effects on mammals.

During the last thirty years a new class of stomach poisons has appeared which has the advantage of being toxic to certain insects but harmless to mammals. This new class of toxins is based on proteins which the cells of *Bacillus thuringiensis* synthesize during their spore forming growth phase. When the larvae of certain insects, especially the larvae of the cabbage butterfly, eat leaves contaminated by these proteins, these proteins act as potent endotoxins.

Recently Ellar et al., (U.S. Pat. No. 4,918,006), incorporated herewith by reference, using genetic engineering techniques, have been able to induce the cells of *E. coli* and *B. subtilis* cultures to produce large amounts of one of the several proteins synthesized by *B. thuringiensis*. This protein can be readily isolated, dissolved in suitable organic solvents, combined with wetting agents and sprayed upon plants. These preparations act as stomach poisons. They are also toxic to mosquito larvae.

Even more recently research workers at the University of Wisconsin have been able by genetic engineering techniques to introduce the plasmids containing the DNA code for this *B. Thuringiensis* protein into russet potato plants. Such plants produce the toxic protein in their leaves. Thus, no need exists for the grower to spray his plants for the control of potato beetles since the leaves are now toxic to any larvae which eat the leaves of untreated plants.

Only two groups of proteins have been proposed as commercially feasible products to control insects, namely the protein of this disclosure, dimercash, and three or four proteins isolated from cultures of the bacterium *Bacillus thuringiensis*. The physical and biological properties of these two classes of proteins are different as are their physiological effects on insects.

The principal protein from *B. thuringiensis* has a molecular weight of about 27,000 Daltons, occurs in the spore as a lipopolysaccharide protein and acts as a cytolytic endotoxin when the protein enters the gut of certain insects. Thus, this protein is a stomach poison and has no contact insecticidal actions in its present form. Crude preparations containing this protein have been used as commercial insecticides by dusting dried cultures of the organism onto the leaves of plants.

By contrast the protein, dimercash described in this disclosure, is a phosphorus containing protein; it is not a lipopolysaccharide protein. It has an amino acid composition which is similar to that of kappa casein. It has a dimer molecular weight of about 38,000 Daltons, is synthesized in mammary glands, and contains two phosphorus atoms.

The pure protein presents no suggestion of contact insecticidal activity when it is used alone; such action only appears when the protein is combined with a membrane transfer agent to form a synergistic mixture. The individual components by themselves show no action against insects at concentrations which are highly toxic when they occur together.

Thus, based on the molecular weights, the amino acid compositions, the sites of formation in cells and their actions on insects, *B. thuringiensis* proteins and the casein derived protein described in this disclosure are unrelated proteins having different physiological and toxicological actions. Their sole points of similarity are a) they both are relatively small proteins, b) they both are lipophilic and c) they both kill insects albeit by entirely different biochemical mechanisms.

The membrane transfer agents include detergents and solvents. Many of these if used in high concentrations may be toxic to insects. However, the proportions employed with dimercash do not visibly affect the insects. Moreover, the membrane transfer agents kill insects by an entirely different biochemical mechanism from that of the insecticidal compositions of this invention.

Insects killed by high concentrations of detergents, for example, die slowly, sluggishly and gently. Some researchers believe that detergents kill insects by blocking the respiratory pores, while others believe that the detergents affect the integrity of cell membranes. By contrast, insects killed by the synergistic mixture described herein, die in a frenzy of uncontrolled and uncoordinated activity. This type of death is typical of classic nerve poisons.

Some examples of commercial nerve toxins, which are toxic to insects, but relatively non-toxic to man, are malathion and parathion. These nerve poisons act by inhibiting the enzyme acetal choline esterase. This enzyme hydrolyzes the natural nerve stimulant, acetal choline, into inactive choline and acetic acid. If the enzyme is blocked by nerve poisons, then acetyl choline accumulates in the tissues and causes uncontrolled stimulation of muscles. This leads to frenzy of uncoordinated activity before death.

Whereas the classical phosphorous based nerve poisons block choline esterase by chemically reacting with serine amino acid at the active site on the choline esterase enzyme, the casein extract of this invention acts as a nerve toxin, when transferred across membranes, by an entirely different mode of action. It appears to affect either directly or indirectly the interaction of the acetyl choline with the receptor protein.

SUMMARY OF THE INVENTION

This invention relates to the method of preparing a lipophilic, calcium linked dimer, free sulfhydryl containing extract of casein, in particular the kappa casein thereof, or casein containing compositions, such as dried skim milk, that comprises contacting the casein with an ($C_1$–$C_4$)alcohol or a ($C_2$–$C_4$) ketone and recovering the extract. This proteinaceous extract is then mixed with an agent that will transfer the protein across normally impermeable membranes to form a synergistic, contact insecticide composition.

This invention also relates to the method of combatting insects and/or slugs comprising applying to an area in need of treatment an insecticidal and/or anti-slug amount of the composition of this invention comprising the lipophilic, proteinaceous extract and a membrane transfer agent in an insecticidal ratio.

Also part of the invention is a kit comprising the synergistic, insecticidal composition of the invention in a sealed container and directions for its application.

The extract and membrane transfer agent may be mixed together in the same container or packaged in separate containers. These components may be in solid or in liquid forms. Diluents, such as buffered aqueous solutions or alcohols, may also be included in the kit.

DETAILED DESCRIPTION OF THE INVENTION

The casein extract of this invention has an amino acid composition which is similar to that of kappa casein. It is a lipophilic, calcium-linked dimer having at least one free sulfhydryl moiety per molecule and contains two phosphorous atoms. It has a dimer molecular weight of about 38,000 Daltons, and is relatively heat stable up to about 85° C. The sulfhydryl moiety forms from a previously unrecognized thioester group in kappa casein.

While it has been found that calcium is necessary to form the dimer bridges between monomers, as well as for effective insecticidal activity, either too much or too little producing a protein that has little or no insecticidal activity, the disclosed methods of preparing the protein extract have been found to produce excellent yields of the desired active product without adjusting the calcium level.

Low cost, simple, almost fool proof methods for preparing the casein extract, having excellent quality, may employ commercial dry skim milk powder as the starting material. The milk may be extracted with a 50–80%, preferably 60–70%, low molecular weight aqueous alcohol or ketone solvent.

The alcohol that may be employed in the extraction method of this invention is preferably a low molecular weight alcohol, such as methanol, ethanol, n-proponal, isopropanol, n-butanol, t-butanol, or 1-isobutanol. The ketone is also preferably low molecular weight, such as acetone, methylethyl ketone or diethyl ketone. However, other alcohols and ketones, as well as other organic solvents, may be used as long as they have lipophilic extracting properties.

Although most commercial extraction operations rarely affect the chemical nature of the extracted material, the extraction operation described in this disclosure is one in which two unexpected, critical reactions occur: 1) a biochemical reaction occurs, namely, the liberation of a free sulfhydryl group, and 2) there is a biophysical reaction with the calcium crosslinking of two monomers of SH-kappa casein to form a biologically active dimer. Thus, what is extracted is a protein product which did not originally exist in the starting raw material.

Pure casein prepared under relatively mild conditions contains no free sulfhydryl groups. Most researchers in this field believe that cysteine in casein molecules occurs as bridging cystine molecules. Only when the protein fractions are intensively manipulated, as shown by Beeby (Biochim. Biophys. Acta 82:418, 1964 ), does a free SH group occasionally appear. Therefore, finding that the very mild conditions used in the present invention produces a free SH group is unexpected. (See Table 1)

The regulation of the proper calcium level is also simple and is automatic. Pure casein, such as commercial Hammarsten casein, is completely soluble in 60% alcohol or acetone. On the other hand casein in the presence of excess calcium ions is completely insoluble in 60% alcohol or acetone. Since commercial dry skim milk powder always has a large excess of calcium ions, ordinary casein cannot be extracted by aqueous organic solvents.

However, kappa casein in its free SH form can form dimers in which calcium ions link the carboxyl groups of two kappa casein groups. This converts an insoluble casein into a form soluble in 66% alcohol or acetone solution. There are at least two calcium bridges per dimer. In contrast to the original insolubility of the calcium casein-complex, dimercash is so soluble in alcohol that even large amounts of alcohol, such as 80–90%, do not immediately precipitate the dimer of this invention at room temperature. Therefore, in the disclosed procedures, dimercash is formed and no need exists for regulating the calcium ion concentration. Although freshly prepared dimercash cannot be precipitated by adding additional alcohol, even if added to a content of about 80%, if the solution is stored in the refrigerator for several days, then the dimercash protein will slowly precipitate from solution. On the other hand, upon addition of acetone of about 80%, there is immediate precipitation of the dimercash. Thus, these products may easily be formulated as solutions, emulsions or pure or diluted solids.

In order to speed up the extraction process, the temperature of the alcohol or acetone may be increased from room temperature to between 50° to 85° C., preferably 55°–75° C. Thus, when 50–65% solution of the alcohol extracting solvent, for example, is employed, hot clear extracts of the casein may be secured, which then may be adjusted to 75 to 85% of the solvent and held at temperatures near freezing to allow slow precipitation of the unique protein.

During commercial extraction of dimercash from dry skim milk powder, any other mild constituents which are soluble in 60–66% alcohol will also be extracted. The principal contaminants are lactose, which may crystallize out during storage, and riboflavin. These generally cause no problem. However, if a pure product is desired, these contaminants can be readily removed by known procedures or as suggested in this disclosure.

The lipophilic, calcium-linked, free sulfhydryl proteinaceous extract may be concentrated, e.g., in a falling film evaporator, and the concentrated suspension dried. e.g., either freeze-dried, spray-dried, or drum-dried, and then optionally ground, e.g., to a powder form. The powder may then be admixed with the membrane transfer agent if the latter is in solid form. Alternatively, the two components may be admixed first and then dried and disintegrated. Still another method of combining the lipophilic proteinaceous extract and the membrane transfer agent is to perform the mixing operation just before the mixture is diluted with water, preferably immediately prior to applying the solution.

The lipophilic, proteinaceous extract admixed with the membrane transfer agent may also be provided as a fine emulsion in water or as a solution in a dilute aqueous alcohol or other organic solvent known for its dissolving ability of lipophilic materials and which will not interfere with the insecticidal activity.

In general, the membrane transfer agent may be an anionic detergent, a cationic detergent, or a non-ionic detergent, among others, as well as mixtures thereof. The specific amount of membrane transfer agent in the composition of the invention preferred for killing insects varies with the detergent. Examples are provided below for typical levels of some common detergents.

A detergent may function as a sole component or as one component of a membrane transfer mixture, yet a wide range of effectiveness exists. The preferred and most effective membrane transfer agents have been found to be amide surfactants including nonionic and amphoteric amides. The most preferred agents include hydrophilic amides of fatty acids, such as N-alkyl fatty acid amides where the fatty acid comprises $C_8$–$C_{22}$ fatty acids that may be further substituted with OH, or one or two ethanol, n-propanol or isopropanol residues or one or more groups such as betaine, among others of similar characteristics.

Particularly preferred membrane transfer agents are N-monoalkanolamine or N-dialkanolamine fatty acid amides, such as N-monoethanolamine or N-diethanolamine fatty acid amides and N-propyl betaine fatty acid amide, particularly those prepared from the coconut oil fatty acids. The fatty acid amides are particularly effective if used in a neutral or slightly alkaline solution. (About pH 6.5–8.5)

Solvents such as dimethylsulfoxide (DMSO) in, for example, a 5–20% solution are good membrane transfer agents. Mixtures comprising a quarternary ammonium detergent and a solvent, such as Arquad S-50 (Soytrimonium chloride and isopropyl alcohol), or hydrophil it amides of fatty acids and phospholipids may also be employed for transferring the lipophilic preteinaceous extract across insect membranes.

Insecticide Assay

The details of the insecticide assay are described in Example 1. For reasons of convenience and ready availability, the insect used in the standard assays described in this disclosure is the American cockroach. This choice is especially advantageous. The cockroach is a large, active insect with a well developed nervous system and with very specific behavior patterns. Thus, in testing a product that is a nerve toxin, the progress of nerve poisoning can be easily monitored. If sedentary insects, such as aphids or scales, or small insects such as ants are used, the nerve toxin action could be overlooked.

When the cockroach is dipped momentarily into a dilute solution of the test solution, a typical sequence of responses occurs. After about 30 seconds the cockroach engages in a frenzy of uncoordinated activity, wildly careening around the container, scrambling up the wall, falling on its back and stumbling because some legs move faster than others. Eventually its frenzy of activity declines as its legs become paralyzed. Paralysis generally starts with the hind legs and progresses to the front legs. The antennae are the last part of the cockroach to become paralyzed. The normal posture of a killed cockroach is the classical spread eagle position with the cockroach having all of its legs spread out at right angles parallel to its body.

A sublethal dose of the dimercash, combined with the appropriate amount of membrane transfer agent frequently so sedated the insect that the antennae could be touched without the insect exhibiting any avoidance reactions. Generally such insects would recover in about an hour with no observable long term ill effects.

Certain membrane transfer agent combinations modified the sequence of paralysis reactions. Instead of assuming the normal flattened position, the cockroach would elevate its body so that it looked like a tarantula spider and would die with all of its limbs rigidly locked in this most unnatural position. Such a dead cockroach could easily be picked up by one leg and placed somewhere else on the table in the same position. Such a change in the response of the insect to different membrane transfer agents or combinations thereof indicates that different agents modify the movement of the casein extract inside the body of the insect.

The Need for a Free Sulfhydryl Group

That the casein extract has a free sulfhydryl group which is essential for its physiological activity is illustrated by the reversible inhibition of the insecticidal activity by mercury. (Table 1) The casein extract was assayed by the test described in Example 1.

TABLE 1

Reversible Effect of Mercury on the Insecticidal Activity

| | Treatment | *RU/ml | % of Original |
|---|---|---|---|
| 1. | Original solution. No treatment | 2,000,000 | 100 |
| 2. | Orig. Sol'n saturated with EtHgCl | 12 | Trace |
| 3. | #2 sol'n plus cysteine crystals | 1,890,000 | 94.5 |

*RU = Roach Units (The reciprocal of the maximum dilution ratio which kills a cockroach within one minute or less.)

The action of cysteine in almost completely reversing the inhibiting effects of mercury is the classical test for biochemically essential sulfhydryl groups.

The Need for a Critical Ratio of Calcium to Protein

That a critical ratio of calcium to protein is necessary for insecticidal activity to be exhibited is illustrated by the data in Table 2. Hammarsten casein is a highly purified casein product prepared by repeated isoelectric reprecipitation. If properly prepared, it contains no calcium ions. However, most commercial preparations of Hammarsten casein contain variable trace amounts of calcium.

TABLE 2

Effect of Calcium on the Insecticidal Activity of Hammarsten Casein Extract*

| Manipulations | RU/mg |
|---|---|
| No Additives | 2.95 |
| 0.46 mg of CaCl/1.84 mg casein | 50.00 |
| 1.63 mg of CaCl/1.84 mg casein | 13.29 |
| 9 mg of Na Oxalate/1.84 mg casein | 0.0 |

This experiment was run to illustrate one specific and limited point, namely, that to form a toxic protein from a casein preparation, either too little or too much calcium ions prevents the formation of the biologically active dimercash.

The data indicate a) that this sample of commercial Hammarsten casein contained a trace amount of calcium which was sufficient to form a small amount of the extract of this invention, b) that if this trace amount of calcium was immobilized by adding sodium oxalate (or in other experiments by dialyzing the casein extensively against EDTA water) that all insecticidal activity disappeared and c) that an optimum level of calcium existed.

The specific insecticidal activity of the best of the samples made from Hammarsten casein is several orders of magnitude lower than that of dimercash prepared by extracting skim milk powder with 60–65% methanol. A definite biochemical reason exists for this difference in results. During the extensive purification procedure used to produce Hammarsten casein, undoubtedly many of the thioester sulfhydryl bonds are broken and later oxidized to form disulfide bonds. Such oxidized casein material can not form dimercash unless the disulfide bonds are selectively reduced.

Effect of Oxidizing Agents on Dimercash

Adding 1 ml of a 3% hydrogen peroxide solution to 50 ml of the dimercash solution having 35,000 RU/ml destroyed all of the insecticidal activity as measured by the standard assay procedure given in Example 1. Adding cysteine crystals did not revive the activity.

The conclusion from this experiment is that the sulfhydryl groups of dimercash, which are critical for activity, were irreversibly oxidized.

Insecticidal Activity of Selected Detergents

The following data are included to show that the action of the detergents in the disclosed formulations differs from the action of these same detergents when used alone at much higher concentrations.

Certain detergents at sufficiently high concentrations also act as insecticides. However, detergents kill insects differently than does the synergistic combination disclosed herein. Also a difference exists in the toxicity rating of a detergent when it is assayed alone and when it is assayed in combination with a suitable concentration of dimercash.

For example, when tested alone at high concentrations, cocamido N-diethanolamine is more toxic than cocamido N-propyl betaine. However, when the detergents (which now function as membrane transfer agents) are combined with the same amount of dimercash then the N-diethanolamide of mixed fatty acids is less toxic than the betaine derivative combination.

The data in Table 3 illustrate the insecticidal activity of several types of detergents. Death from high concentrations of these detergents was gradual and was not accompanied by the frenzied activity typical of nerve poisons.

TABLE 3

Insecticital Action of Certain Commercial Detergents When Assayed Without Dimercash

| Commerical Name | Chemical Name | Non Toxic at mg/ml | Toxic* at mg/ml |
|---|---|---|---|
| Cocamido DEA | N-diethanolamine FAA | 1.25 | 3 |
| "Varion" CADG-HS | N-propyl betaine FAA | 5.00 | 10 |
| Cocamido MEA | N-monothanolamine FAA | 12.5 | 16** |
|  | Ethoxylated sorbitol hexa FA | 6 | 10 |
| Quarternary FAA | Quarternary trimethyl FAA | 10 | ? |
| "Tween 80" | Polyethylene sorbitan oleate | 10 | ? |
| "Span" | Sorbitan monostearate | 10 | ? |
| "Dreft" | Na lauryl sulfate | 10 | ? |
|  | Phospholipid | 50 | ? |
| DMSO | Dimethylsulfoxide | 75% | ? |

FA = Fatty Acid
FAA = Fatty Acid Amide
*Death was not caused by a neurotoxic reaction. At high concentrations of detergent solutions, the insects became sluggish and eventually died. In contrast to the sudden and easily detected death from a nerve toxin, death from excess detergent was so slow and gradual that determining the exact time of death was difficult.
**The detergent was poorly dispersible in water. Hence, this figure is only approximate.

Effect of a Membrane Transfer Agent on Insect Toxicity

Since the extracted protein of this invention is too large to cross membranes, dipping cockroaches into pure solutions does not harm the insects; the protein remains harmlessly on the outer surface of the insects. For the protein to kill the insect it must be combined with some agent which will transfer the intact protein across the normally very effective membrane barrier which protects the interior of the insect from harmful materials from outside the insect.

At least two classes of materials can economically accomplish this difficult to achieve objective, namely, certain detergents and certain solvents, such as dimethylsulfoxide. Regardless of their other properties or their standard classification, if they can transfer molecules which normally cannot cross critical cell membranes, they function as cell membrane transfer agents rather than as simple wetting, spreading agents in the case of detergents or as an amphoteric solvent in the case of dimethylsulfoxide.

The data in Table 4 illustrate the effectiveness of certain detergents which also function as membrane transfer agents in converting an innocuous protein into an extraordinarily potent nerve poison for insects.

TABLE 4

Comparison of Several Detergents as Membrane Transfer Agents for a Constant Amount of Dimercash Protein

| Exp # | Detergent | Conc. | RU(Roach Units) |
|---|---|---|---|
| 1 | Cocamide N-DEA | 4.0 mg/ml | 1,000 RU/mg protein |
|  | Cocamido N-propyl betaine | 2.0 mg/ml | 50,000 RU/mg protein |
| 2 | *Tween 80 | 4.4 mg/ml | Discomfort non toxic |
|  | **Arquad S-50 | 5.0 mg/ml | 20,000 RU/M/Protein |
|  | Cocamido N-propyl betaine | 2.0 mg/ml | 40,000 RU/mg protein |

*Polyethylene sorbitan oleate
**Quaternary ammonium detergent (Soytrimoniumchloride and isopropyl alcohol) This material is normally sold for disinfecting surfaces.

In these experiments the concentration of the dimercash was kept constant and the concentration of the detergent increased until the combination was toxic.

The critical amount of membrane transfer agent which must be combined with the dimercash is a function not of the protein concentration but of the area of membrane surface which must be covered when the diluted mixture is sprayed on plants or insects. The solution which contacts the insect must have a sufficient number of molecules to modify the insect membrane so that the dimercash can enter into the body of the insect.

In transferring dimercash across insect membranes for killing cockroaches, there may be employed about 2 mg of cocamido-propyl betaine per ml of the mixture's applied solution. For cocamido N-diethanolamine the amount is about 4 mg per ml of the applied solution. However, it is important to note that different insects will require different amounts of detergent. Nevertheless, with the information disclosed as a starting point, anyone skilled in the art can readily devise different formulations, which when diluted according to the directions will cause the desired results.

In general, the membrane transfer agent may be employed in amounts of about 1–25 mg of detergent to 1 ml of solution, or 1–25% solutions of solvents with the RU(Roach Units) of dimercash of about 50 to 50,000RU per ml of applied solution. However, as above pointed out these proportions may vary according to the transfer agent employed, area or matter to be treated as well as the results desired. The most effective agents and proportions may be readily determined by the disclosed methods.

What is particularly important is that the detergent, solvent or mixtures thereof be present in such minimum concentrations as to change the permeability of the impermeable membrane layers. Once this has been determined, the dimercash can range from 50 to 50,000 RU or more. Reasons for increasing the amount of dimercash are:
1. Longer effective toxicity under unfavorable environmental conditions.
2. More potent action against particularly resistant insects.
3. Longer shelf life for the solution.

EXAMPLES

Example 1

Assay for Insecticidal Activity

The standard assay procedure consisted of preparing ten 1:5 serial dilutions of the sample in 8 ml of distilled water. To each tube containing the diluted sample 2 ml of 10 mg/ml cocamido N-propyl betaine solution were added, giving a total volume of 10 ml. Testing started with the most dilute solution and continued with more concentrated solutions until finally a dilution was reached which killed the cockroach within one minute or less by a classical nerve toxin reaction.

With this concentration as the approximate toxic dose, a new dilution series was prepared in the vicinity of the toxic dose but making the serial dilutions much smaller. Generally 1:2 serial dilutions were used for the final assay.

Each dilution was tested by pouring the 10 ml of solution into a 250 ml plastic cup, dropping one cockroach therein and immediately removing the wetted cockroach for transfer to a dry beaker for observation. A dilution was considered toxic if the cockroach died a classical nerve poison death within one minute or less.

The insecticidal potency of each sample is expressed as the reciprocal of the dilution which kills the cockroach by a nerve toxin reaction within one minute or less.

The stock membrane transfer agent contained 10 mg of cocamido N-propyl betaine (VARION CADG-HS from Sherex Chemical Company) adjusted to pH 7.0.

Example 2

Extraction of Dimercash from Dry Skim Milk Powder 100 g skim milk powder was slurried with one liter of 65% aqueous methanol and held for one half hour. The clear supernatant was decanted and the residue was centrifuged to remove the small amount of remaining solution. The semi-dry residue was then resuspended in one liter of fresh 65% methanol solution and the extraction process continued. The reextraction process was continued an additional two times.

All of the extracts were held in the refrigerator and then processed to form dry powders by a process involving concentration on a thin film evaporator or low temperature vacuum evaporation and freeze drying. The properties of each fraction are described in Table 5.

TABLE 5

Recovery of Dimercash in Successive Extractions of Skim Milk Powder with 65% Methanol

| Fraction | Weight g | RU/mg | Total RU (/1000) | % of Total RU Recovered |
|---|---|---|---|---|
| Original powder Extract 1 (Reworked) | 100 | 3 | 300 | 0.024 |
| Cold precipitate | 8.74 | 100,000 | 874,530 | 70.0 |
| Supernatant | 2.29 | 475 | 1,088 | 0.087 |
| Extract 2 | 7.643 | 25,602 | 195,689 | 15.7 |
| Extract 3 | 5.833 | 30,000 | 175,000 | 14.0 |
| Extract 4 | 4.353 | 574 | 2,500 | 0.2 |
| Total Extracted | 28.85 | | 1,248,807 | 100.0 |

Even though the methanol concentration was the same in all four extractions, the first extraction, because the dry skim milk powder absorbed about 400 g of water for each 100 g of dry skim milk powder, actually had a methanol concentration which was considerably higher than 65%. During the several weeks cooling-holding period a precipitate formed from this originally clear solution. A rework of this precipitate indicated that this precipitate was the most potent source of dimercash. Although some activity was lost during the concentration and freeze drying process, this method produces an eminently suitable product for those applications which require a dry, purified product.

Example 3

Recovery of Dimercash by Extracting Skim Milk Powder with Aqueous Acetone Solutions 50 g of dry skim milk powder were suspended in 500 ml of a 66% aqueous acetone solution and the mixture stirred for one half hour and then centrifuged. To the supernatant solution an equal volume of acetone was added, the precipitate was recovered by contrifuging and the precipitate was dried in a vacuum oven. A second extraction with 66% acetone solutions was made of the residual semidry powder from the first extraction. To the clear supernatant solution, obtained by centrifuging the slurry, an equal volume of acetone was added. The precipitate, which was recovered by centrifuging was dried in a vacuum oven. The weight and insecticidal activity recovery, measured as in Example 1, is shown in Table 6.

TABLE 6

Recovery of Dimercash from Skim Milk Powder by Aqueous Acetone Extraction

| Fraction | Weight g | RU/mg | Total RU (/1000) | % Recovery |
|---|---|---|---|---|
| Original | 50.0 | 3 | 150 | 0.04 |
| First Acetone Ext. | | | | |
| Acetone Ppt. | 15.95 | 16,613 | 264,977.35 | 76.2 |
| Ac. Supernt. | 5.17 | 8,507 | 43,981.19 | 12.6 |
| Second Ac. Ext. | | | | |
| Acetone Ppt. | 4.81 | 8,073 | 38,831.67 | 11.2 |
| Ac.Supernt. | 18.0 | 1 | 18 | 0.005 |
| Total Recovery | 43.93 | | 347,807.67 | |
| Usable Product | 25.93 | 11,064 | 347,789.67 | |

Although the recovery and the specific activity are about half that of the preceding recovery technique, the product is eminently acceptable. The loss of activity occurred during the drying step, the vacuum oven drying causing a greater loss in activity than did the freeze drying.

Example 4

Recovery of Dimercash from Skim Milk Powder by Heated Aqueous Methanol Solution

This example differs from the examples 2 and 3 in that the dimercash is extracted and used in a methanol solution. It represents the simplest method for producing a commercial extract for those applications where a liquid solution of the protein is preferred over a solid product.

To 15 lbs of dry skim powder, 9 gallons of MeOH and 9.5 gallons of 65° C. water were added. After stirring the suspension for a half an hour, the solution was allowed to settle and the clear supernatant solution decanted. To the insoluble material 15 gallons of hot (55° C.) 66% aqueous methanol were added, the solution stirred for 0.5 hours and then allowed to settle overnight. The clear supernatant solution was decanted from the insolubles and the supernatant solution combined with the first supernatant solution.

The RU potency of the combined solution was 275,000 RU/ml. The solution was suitable for the preparation of commercial contact insecticides as described in Example 6 and for certain other commercial applications.

Example 5

Effect of Additives on the Recovery of Biological Activity after Concentrating the Solution 20 g. skim milk powder were extracted with a single 200 ml 50% aqueous acetone solution containing various additives. The suspension was stirred for a half an hour, centrifuged and the supernatant solution concentrated on a thin film evaporator and the solution assayed.

The results are shown in Table 7.

TABLE 7

Effect of Additives

| | Test Additive | pH | Recovered RU per g of skim milk |
|---|---|---|---|
| 1 | 1% dimethylsulfoxide (DMSO) | 6.2 | 2200 |
| 2 | 0.5% cocamido N-diethanolamine | 6.5 | 1940 |
| 3 | NH$_4$OH | 8.8 | 605 |
| 4 | Acetic acid | 4.2 | 1000 |
| | The original powder contained | | (85) |

Example 6

Preparation of Insecticidal Mixture

The critical part of the formulation requires sufficient membrane transfer agent so that the solution which is applied to the plant or animal contains at least a certain minimum amount of membrane transfer agent. The precise amount will be determined by the membrane transfer agent that is chosen. For example cocamido N-propyl betaine this is about 1.5–2.0 mg/ml and for cocamido N-diethanolamine this is about 4 mg/ml.

The amount of dimercash should be about 50 RU per ml of applied solution. However, since this component is less expensive than the membrane transfer agent, using larger amounts provides a measure of safety.

An additional example, among the many possibilities that may be readily formulated, is as follows:

Four gallons of water was added to 25 pints of Varion (a 35% solution of cocamido N-propyl betaine made by Sherex) and adjusted to pH 7. Then 23 pints of the dimercash prepared by the method of Example 4, was added thereto. This gave 10 gallons of a concentrated contact insecticide.

The concentrated product was diluted 1:50 before using. At this dilution the concentration of cocamido N-propyl betaine was 2 mg/ml and the RU of the dimercash approximately 8000 RU/ml. Both of these figures are within the recommended values with the protein RU being in a considerable excess.

Example 7

Effect of the Insecticide on Insects, Animals and Plants

One pint of the concentrated insecticide solution from Example 6 was diluted to 6 and ¼ gallons. This solution was tested against various insects and plants.

Spraying rose bushes and other plants gave a quick kill of various species of caterpillars, aphids, mites and scale. Caterpillars which were hit by the spray immediately began writhing and dropped from the leaves. They died on the ground.

The control of large, active flying insects, such as Japanese beetles, was only fair. If the beetles could be hit and wetted, they died. However, those beetles which received only a small amount of spray, immediately flew away before they could be completely wet with the spray.

Snails and slugs took about 20 minutes to die after they were wetted with the spray. During the time they excreted copious amounts of mucous.

Dogs given a shampoo with this mixture were completely freed of fleas. Some of the fleas jumped off the dog before they were wetted with the shampoo. They could then be killed by spraying area with the solution.

The invention now being fully described, it will be apparent to one of ordinary skill in the art that many changes and modifications can be made there without departing from the spirit or scope of the invention as set forth herein.

I claim:

1. A relatively heat stable, up to about 85° C., lipophilic, phosphorous containing proteinaceous extract of kappa casein having neurotoxic, insecticidal properties when transferred across the membranes of insects, prepared from a kappa casein containing material with an extracting agent comprising a 50–80% solution of a $C_1$–$C_4$ alcohol or a $C_2$–$C_4$ acetone and recovering said extract, which is a calcium linked dimer with free sulfhydryl groups having a dimer molecular weight of about 38,000 Daltons.

2. The extract of claim 1, wherein the alcohol is selected from the group consisting of methanol, ethanol, n-propanol, isopropanol, l-isobutanol. n-butanol and t-butanol.

3. The extract of claim 1, wherein the acetone is selected from the group consisting of acetone, methyl ethyl ketone and diethyl ketone.

4. The extract of claim 1 wherein the extracting agent is a 60–70% aqueous solution of the alcohol or the acetone.

5. The extract of claim 1, wherein the temperature of the extracting agent is increased from room temperature to between 50°–85° C.

6. The extract of claim 5, wherein the extracting agent is a 60–70% aqueous methanol solution and a hot clear extract is recovered, the alcohol content is adjusted to 75–85%, and held at near freezing for precipitation of the extract.

7. A synergistic, neurotoxic, insecticidal composition consisting essentially of
   a) the extract of claim 1 having a potency of 50–50,000 Roach Units, and
   b) a membrane transfer agent comprising an amide detergent or dimethyl sulfoxide in an amount that is not toxic to insects but is effective to transfer the extract across normally impermeable insect membranes.

8. The composition of claim 7, wherein the membrane transfer agent is a nonionic or amphoteric fatty acid amide.

9. The composition of claim 7, wherein the membrane transfer agent is cocamido N-propyl betaine.

10. A syngeristic, neurotoxic, insecticidal composition consisting essentially of
    a) the extract of claim 1 having a potency of approximately 50–50,000 Roach Units, and
    b) a membrane transfer agent comprising an amide detergent or dimethyl sulfoxide in an amount that is not toxic to insects but is effective to transfer the extract across normally impermeable insect membranes.

11. The composition of claim 10 in powder form.

* * * * *

UNITED STATES PATENT AND TRADEMARK OFFICE
CERTIFICATE OF CORRECTION

PATENT NO. : 5,591,443
DATED : January 7, 1997
INVENTOR(S) : Heinicke

It is certified that error appears in the above-identified patent and that said Letters Patent is hereby corrected as shown below:

Claim 10,
Make it dependant on claim 6.

Signed and Sealed this

Eleventh Day of December, 2001

Attest:

*Attesting Officer*

NICHOLAS P. GODICI
*Acting Director of the United States Patent and Trademark Office*